(12) United States Patent
Fulton et al.

(10) Patent No.: US 11,109,661 B2
(45) Date of Patent: Sep. 7, 2021

(54) SYSTEM, DEVICE AND METHOD OF FACIAL REMODELING

(71) Applicant: New You Lift, LLC, Grand Junction, CO (US)

(72) Inventors: Richard Eustis Fulton, Grand Junction, CO (US); German Todorov, Atlanta, GA (US)

(73) Assignee: New You Lift, LLC, Grand Junction, CO (US)

( * ) Notice: Subject to any disclaimer, the term of this patent is extended or adjusted under 35 U.S.C. 154(b) by 0 days.

(21) Appl. No.: 15/863,174

(22) Filed: Jan. 5, 2018

(65) Prior Publication Data

US 2018/0125205 A1    May 10, 2018

Related U.S. Application Data

(63) Continuation-in-part of application No. 15/660,809, filed on Jul. 26, 2017, now abandoned.

(60) Provisional application No. 62/443,985, filed on Jan. 9, 2017, provisional application No. 62/366,891, filed on Jul. 26, 2016.

(51) Int. Cl.
| | | |
|---|---|---|
| *A61K 8/63* | (2006.01) | |
| *A45D 44/00* | (2006.01) | |
| *A45D 44/22* | (2006.01) | |
| *A61K 8/02* | (2006.01) | |
| *A61K 8/9789* | (2017.01) | |
| *A61K 8/9794* | (2017.01) | |
| *A61K 8/49* | (2006.01) | |
| *A61K 8/64* | (2006.01) | |
| *A61K 8/60* | (2006.01) | |
| *A61K 8/35* | (2006.01) | |
| *A61K 8/34* | (2006.01) | |
| *A61K 8/37* | (2006.01) | |
| *A61K 8/368* | (2006.01) | |
| *A61K 8/67* | (2006.01) | |
| *A61K 8/73* | (2006.01) | |
| *A61K 8/44* | (2006.01) | |
| *A61K 8/81* | (2006.01) | |
| *A61Q 19/08* | (2006.01) | |
| *A61K 8/92* | (2006.01) | |
| *A61M 35/00* | (2006.01) | |

(52) U.S. Cl.
CPC ........... *A45D 44/002* (2013.01); *A45D 44/22* (2013.01); *A61K 8/0212* (2013.01); *A61K 8/342* (2013.01); *A61K 8/345* (2013.01); *A61K 8/35* (2013.01); *A61K 8/368* (2013.01); *A61K 8/37* (2013.01); *A61K 8/375* (2013.01); *A61K 8/44* (2013.01); *A61K 8/498* (2013.01); *A61K 8/60* (2013.01); *A61K 8/63* (2013.01); *A61K 8/64* (2013.01); *A61K 8/678* (2013.01); *A61K 8/731* (2013.01); *A61K 8/735* (2013.01); *A61K 8/8147* (2013.01); *A61K 8/922* (2013.01); *A61K 8/9789* (2017.08); *A61K 8/9794* (2017.08); *A61M 35/10* (2019.05); *A61Q 19/08* (2013.01); *A61M 2205/0216* (2013.01); *A61M 2210/0606* (2013.01)

(58) Field of Classification Search
CPC ...... A61K 8/0212; A61K 8/63; A61K 8/9789; A61K 8/9794; A61K 8/498; A61K 8/64; A61K 8/60; A61K 8/35; A61K 8/345; A61K 8/342; A61K 8/375; A61K 8/368; A61K 8/678; A61K 8/731; A61K 8/735; A61K 8/44; A61K 8/922; A61K 8/37; A61M 2210/0606; A61M 2205/0216; A45D 44/002; A45D 44/22; A61Q 19/08
See application file for complete search history.

(56) References Cited

U.S. PATENT DOCUMENTS

| | | | | |
|---|---|---|---|---|
| 1,678,970 | A | * 7/1928 | Arlen | A45D 44/22 606/204.35 |
| 2,728,339 | A | * 12/1955 | Elmhirst | A45D 44/22 2/206 |
| 4,150,418 | A | 4/1979 | Berbeco | |
| 4,201,433 | A | * 5/1980 | Caldwell | H01R 4/646 439/98 |
| 4,249,226 | A | 2/1981 | Westberg et al. | |
| 4,642,912 | A | 2/1987 | Wildman et al. | |
| 4,926,570 | A | 5/1990 | Fohst | |
| 5,004,425 | A | 4/1991 | Hee | |
| 5,091,996 | A | * 3/1992 | Kirby | A01M 31/00 2/171 |
| 5,233,769 | A | 8/1993 | Weber | |
| 5,576,924 | A | 11/1996 | Hee | |
| 5,599,546 | A | 2/1997 | Klein | |
| 5,935,596 | A | 8/1999 | Crotty et al. | |
| 6,003,247 | A | 12/1999 | Steffe | |

(Continued)

FOREIGN PATENT DOCUMENTS

| | | | |
|---|---|---|---|
| CN | 204121448 U | * 1/2015 | |
| GB | 191107396 A | * 10/1911 | ............. A61H 15/00 |
| KR | 20010094548 A | * 11/2001 | |

*Primary Examiner* — Ali Soroush
(74) *Attorney, Agent, or Firm* — Schmeiser, Olsen & Watts LLP (57) ABSTRACT

A system for facial remodeling, including a device and methods of use, is provided. The system combines a topical composition configured to restore elastin, hyaluronan, or both to the skin and subcutaneous soft tissues of the face and neck with a facial mask to support and, in some embodiment, compress the tissue, to enhance and preserve the tissue remodeling effects of the composition. Some versions of the facial mask device include a means for electrically grounding the skin and soft tissues of the face, neck, and head, wherein the user receives local tissue benefits of "earthing." In some versions, the facial mask is formed by combining different elements and configurations to compress skin and underlying soft tissue, bias areas of skin and soft tissue in a cranial direction, and ground the face, head, and neck tissues.

15 Claims, 6 Drawing Sheets

(56) References Cited

U.S. PATENT DOCUMENTS

| | | | |
|---|---|---|---|
| 6,237,256 | B1 | 5/2001 | Maki et al. |
| 6,682,779 | B1 | 1/2004 | Wefringhaus et al. |
| 6,707,659 | B2 | 3/2004 | Hee |
| 7,055,266 | B2 | 6/2006 | Elsey |
| 7,212,392 | B2 | 5/2007 | Walker et al. |
| 7,609,503 | B2 | 10/2009 | Hee |
| 7,724,491 | B2 | 5/2010 | Ober et al. |
| 8,257,385 | B2 * | 9/2012 | Karnwie-Tuah ....... A45D 44/22 606/204.35 |
| 9,101,195 | B2 * | 8/2015 | Owoc ................... A45D 44/22 |
| 9,161,958 | B2 | 10/2015 | Mahmood et al. |
| 2004/0219124 | A1 | 4/2004 | Gupta |
| 2004/0161435 | A1 | 8/2004 | Gupta |
| 2004/0173220 | A1 | 9/2004 | Harry |
| 2009/0130040 | A1 | 5/2009 | Jonchiere |
| 2014/0356295 | A1 * | 12/2014 | Gerardi ................. A61K 36/81 424/43 |
| 2017/0027878 | A1 | 2/2017 | Carullo et al. |
| 2017/0216584 | A1 * | 8/2017 | Chun .................... A61N 1/303 |

* cited by examiner

SYSTEM, DEVICE AND METHOD OF FACIAL REMODELING

CROSS REFERENCE TO RELATED APPLICATION

This application is a continuation-in-part of U.S. patent application Ser. No. 15/660,809 filed Jul. 26, 2017 and entitled "Proprioceptive Enhancement Device and Method of Use," the disclosures of which are hereby incorporated entirely herein by reference. Application Ser. No. 15/660,809 claims priority to United States Patent Application No. 62/366,891, filed Jul. 26, 2016 and entitled "Device and Method of Enhancing Postural Stability," and additionally claims priority to U.S. Patent Application No. 62/443,985, filed Jan. 9, 2017 and entitled "Devices and Methods for Enhanced Electrical Conductivity and Postural Stability,", the disclosures of which are hereby incorporated entirely herein by reference.

BACKGROUND OF THE INVENTION

Technical Field

This invention relates to systems, devices and methods for facial remodeling. Specifically, embodiments of the invention relate to a system combining a device and topical tissue remodeling composition for toning skin and soft tissues of the face.

State of the Art

As the world's population ages, there is a demand for products and methods which may either delay the aging process or at least cause the skin, particularly of the face, to appear more youthful. There are literally thousands of products addressing this huge market including moisturizers, lotions, anti-aging creams and serums, cleansers and exfoliators to name just some. Many of these products are very expensive and provide only marginal benefit to the user. They may contain chemicals or substances directed to a specific action. For example, retinoids are utilized in anti-aging creams or serums as they increase cell turnover and may enhance collagen formation while moisturizers may contain glycerin and/or hyaluronic acid. Antioxidant creams may contain niacinamide or other substances that may help reduce the signs of sun damage while others contain substances that protect the skin from being damaged by the sun.

Skincare products frequently contain multiple ingredients to address different issues, but almost uniformly they consist of substances that must be applied to the skin and absorbed into the epidermal and dermal layers of the skin. Despite the existence of very little evidence-based data that support the relative effectiveness of many of these compositions and methods, they are widely utilized as they are non-invasive, mostly safe, have limited side effects that usually can be corrected by discontinuing use, can be applied by the user, and gives the user the feeling that they are being proactive about their appearance.

At the other end of the spectrum of skin care are laser treatments, micro-needling of the skin, injection of bulking agents, paralytic neurotoxins, and other substances, and plastic surgery amongst other alternative means of treating facial skin and tissues. These latter methods are more invasive, much more costly and come with varying periods of recovery and negative side effects, all of which may be objectionable to the consumer and may dissuade the utilization of these methods.

Accordingly, what is needed is a treatment which combines a tissue remodeling composition or formulations of a self-applied topical skincare product with at least one other non-invasive modality having a physical effect on the tissues. Also missing from this array of skin treatments is a system combining a physical device configured to affect tissues and a topical composition that collectively work together to enhance the individual effect of one another in a non-invasive manner.

SUMMARY OF THE INVENTION

Embodiments of the present invention include a mask device for grounding tissues of the face combined with a topical tissue remodeling composition.

Disclosed is a system of facial remodeling comprising a facial mask having a first lifting strap; a tissue remodeling composition, wherein the facial mask is configured to support a facial tissue treated with the tissue remodeling composition.

In some embodiments, the facial mask comprises a grounding member coupled to the first lifting strap. In some embodiments, the facial mask comprises an ear section coupled to the first lifting strap; and a second lifting strap coupled to the ear section, wherein the first lifting strap and the second lifting strap are coupled together by the ear section.

In some embodiments, the facial mask comprises a grounding member coupled to the facial mask. In some embodiments, the facial mask comprises a grounding member coupled to the second lifting strap.

In some embodiments, the facial mask comprises an elastomeric element. In some embodiments, the first lifting strap comprises an elastomeric element.

In some embodiments, the remodeling composition comprises an elastin-promoting compound; a hyaluronan-promoting compound; and a topical delivery vehicle.

In some embodiments, the elastin-promoting compound is at least one compound selected from the group of compounds consisting of: a ruscogenin at a concentration in a range between about 0.5 percent and 3.0 percent; a dill seed extract at a concentration in a range between about 1 percent and about 5 percent; and a dill seed oil at a concentration in a range between about 1 percent and 5 percent. In some embodiments, the elastin-promoting compound is selected from the group of elastin-promoting compounds consisting of: *Ruscus aculeatus* extract; epigallocatechin-3-gallate; white tea extract; green tea extract; micronized purified flavonoid fraction; *Hedera helix* extract; hederagenin; palmitoyl pentapeptide-4; palmitoyl oligopeptide; and palmitoyl-tetrapeptide-7.

In some embodiments, the hyaluronan-promoting compound is selected from the group of hyaluronan-promoting compounds consisting of: glucosamine, palmitoyl pentapeptide-4; palmitoyl oligopeptide; palomitoyl-tetrapeptide-7; and ethoxyheptyl bicyclooctanone.

In some embodiments, the topical delivery vehicle is selected from the group of topical delivery vehicles consisting of: water; glycerin; cetyl alcohol; coconut oil; olive oil; jojoba oil; glyceryl stearate; a paraben; sodium benzoate; vitamin E; hydroxymethyl cellulose; hyaluronic acid; propylene glycol; disodium EDTA; and a carbomer.

Disclosed is a facial mask comprising a first lifting strap; a grounding means; and a compression means.

In some embodiments, the facial mask comprises a second lifting strap coupled to the first lifting strap. In some embodiments, the first lifting strap is configured to support a skin tissue overlying a zygomatic eminence. In some embodiments, the second lifting strap is configured to support a skin tissue overlying a neck region.

Disclosed is a method of facial remodeling comprising steps applying a topical tissue remodeling composition to skin; and donning a facial mask.

In some embodiments, the method further comprises a grounding step, wherein the facial mask is grounded to a grounding means. In some embodiments, the method further comprises a biasing step, wherein the facial mask biases a facial soft tissue in a cranial direction. In some embodiments, the method further comprises a compressing step, wherein a facial soft tissue is compressed.

The foregoing and other features and advantages of the present invention will be apparent from the following more detailed description of the particular embodiments of the invention, as illustrated in the accompanying drawings.

DETAILED DESCRIPTION OF EMBODIMENTS OF THE INVENTION

The foregoing application describes a system, device, and methods of use for facial remodeling. The system employs a facial mask for compressing and supporting facial tissues in conjunction with a composition to promote restoration of elastin and hyaluronan, provided with a delivery vehicle in a topical preparation.

Various embodiments of the device include a facial mask, which, in some embodiments, includes combinations of different elements and configurations for compressing skin and underlying soft tissue, cranially biasing areas of skin and soft tissue, and grounding the face, head, and neck tissues.

It is an object of this invention to provide one or more substances that may be topically applied by the user along with one or more non-invasive physical means of enhancing the appearance of facial tissues. Elastin is a highly elastic protein that coils and recoils similar to a spring within the elastic fibers of skin and connective tissue and is mostly responsible for the elasticity of structures. It functions in tissues with collagen. As one grows older, elastin production diminishes as elastin degradation accelerates. Combined with gravity, many tissues, including facial skin and tissue, begin to sag in a continual process as the tissue is unable to regain or rebound to the youthful appearing shape over years of stretching and contracting. Applying an elastin-stimulating substance or an elastin protecting substance to tissues and elastin fibers which are already stretched will have limited, if any, benefit. Applying an elastin stimulating substance or an elastin protecting substance to tissues that are supported and not stretched may be much more effective as the elastin fibers may be repaired in their "coiled" or un-stretched configuration. The result will be elastin fibers which function better and provide more elasticity to the tissues and which allow less sagging of tissues.

Some embodiments comprise a device configured to support facial tissues while the substance(s) is being absorbed into the tissues. Some embodiments of the present invention comprise a substance or substances which stimulate elastin production, prevent elastin degradation, or both. Hence, if the elastin fibers are stimulated or protected while the tissues containing them are being maintained in a non-stretched condition, skin and tissue elasticity will be enhanced.

As used herein, the term "lifting" means biasing an area of skin, or an area of skin and soft connective tissue underlying the skin, in a cranial direction. This is independent of whether the user is sitting or standing, wherein the cranial direction is "up." Lifting/biasing skin and soft tissue is caused to happen in a cranial direction independent of orientation of the face, whether the user is supine, sitting, standing, or in any other position. "Cranial" is an anatomic relational term meaning towards the top of the head. It is the opposite of "caudal," meaning towards the feet. Cranial, therefore, means towards the head and away from the feet.

In some embodiments, the device is a facial mask comprising a first lifting strap that elevates the cheek tissues and is secured to the face by one of several means configured to removably attach the facial mask to the face. In some embodiments, the facial mask device comprises a second lifting strap that supports the tissues beneath the chin, the jowls, the periorbital tissues or other tissues as well. The facial mask may be constructed of any number of materials, but preferably the mask comprises an elastic component to bias facial skin and tissue upward—toward the scalp—under a condition wherein the mask is secured to the user's head. Utilization of this system of elastin stimulating or protective/reparative substances along with a physical lifting means to support the tissues while the substance(s) are acting may be done while the user is sleeping, wherein there is a prolonged period of combined physical support and tissue lifting with elastin stimulation and/or protection/repair.

Substances that may be utilized with the facial mask device to enhance elastin production or repair and stabilize existing elastin and substances which may enhance the production or repair and stabilize hyaluronan. Hence, three methods of effecting skin remodeling and change may employ 1) the physical lifting of tissues by a supportive lifting strap, 2) substances to enhance production of critical components of a facial tissue and/or inhibit their degradation, and 3) the healing and capillary blood flow enhancing features of grounding the facial tissues.

A method of firming and tightening mature skin may involve achieving an increase in the skin content of [primarily] elastin and [secondarily] hyaluronan (aka hyaluronate, hyaluronic acid), both of which decline with age. It involves (1) synergistic stimulation of elastin synthesis and inhibition of elastin degradation, and (2) synergistic stimulation of hyaluronan synthesis with inhibition of hyaluronan degradation.

The formation of elastic fibers in the skin consists of several stages that include (1) the production of tropoelastin by fibroblasts, (2) enzymatic crosslinking of tropoelastin yielding elastic microfibrils, (3) microfibril assembly and elastin accretion and, finally, (4) development, anchoring and maturation of elastic fiber that becomes an integral part of the skin matrix. This process occurs in the spatial context of the skin matrix consisting of a variety of biopolymers and structures influencing all of the above steps, but especially steps 3 and 4. In fact, the skin matrix provides a grid guiding microfibril assembly and anchoring of the developing elastic fibers, thus affecting their eventual spatial positioning in the skin. Therefore, the physical state of the skin matrix during the formation of new elastic fibers affects the position and ultimate effect of the newly developed fibers on the skin. In particular, if the skin matrix is compressed during new elastic fiber development, the elastic fiber will be deposited and anchored in such a way as to stabilize the more compressed state of the skin matrix, yielding a greater skin tightening effect.

Compressing the skin matrix during elastic fiber development provides an opportunity to combine stimulation of elastin synthesis with skin matrix compression via mechanical soft tissue lifting. Simply put, stimulating the formation of elastin while the tissues are supported, or compressed in a lifted, non-stretched configuration, will improve the elastic properties of the skin particularly by enhancing the elastin assembly, placement, and anchoring on the microfibrils so that the resulting elastic fibers have more lifting ability than if they were formed or repaired while stretched out in a non-supported elongated configuration. Degraded elastin is comparable to a metal spring which has been stretched for years with the resultant elongation and loss of its ability to contract back into a spiral, spring like configuration. Repairing the spring's elasticity by heat treating the metal of spring may involve compressing the spring prior to the heat treatment to restore the original shape of the spring. The lifting means of the current invention supports or compresses upward the tissues of at least one part of the facial tissues so that at least one of the repair or stimulation of the synthesis of elastin and elastic fibers may result in a greater skin tightening effect which reduces the sagging of skin and tissues.

Increasing the amount of elastin in the skin may be achieved by using a topically applied formulation containing agent(s) that increase the biosynthesis of elastin, such as, but not limited to, aqueous dill seed extract and/or dill seed oil and ethoxyheptyl bicyclooctanone and agent(s) that decrease degradation of elastin either by directly inhibiting elastase and related matrix metalloproteinases (MMP-s), such as, but not limited to, extract of *Ruscus aculeatus* (aka butchers broom) or purified ruscogenins isolated from *Ruscus aculeatus* and Epigallocatechin-3-gallate (EGCG). Other substances that act by shielding elastin from contact with elastase and related MMPs, include white tea extract, Green tea extract, micronized purified flavonoid fraction (MPFF) (diosmin+hesperidin), Extract of *Hedera helix* (a.k.a. common ivy) or purified hederagenin isolated from *Hedera helix*, skin matrix derived/related peptides, such as palmitoyl pentapeptide-4 (MATRIXYL) and palmitoyl oligopeptide & palmitoyl-tetrapeptide-7 (MATRIXYL 3000).

Increase in the hyaluronan skin content is achieved by using a topically applied formulation containing agent(s) that increase the biosynthesis of hyaluronan and may include glucosamine, skin matrix derived or related peptides, such as palmitoyl pentapeptide-4 (MATRIXYL) and palmitoyl oligopeptide & palmitoyl-tetrapeptide-7 (MATRIXYL 3000), and ethoxyheptyl bicyclooctanone, among others.

Agents that decrease degradation of hyaluronan (e.g. by inhibiting hyaluronidase and related enzymes) may include Extract of *Aesculus hippocastanum* (a.k.a. horse chestnut) or escin isolated from *Aesculus hippocastanum* and MPFF, among others.

One or more of the substances listed herein above are combined to into a tissue remodeling composition. In some embodiments, the tissue remodeling composition is utilized with the supportive lifting strap and/or grounding.

In some embodiments, the composition comprises active ingredients including: either ruscogenins at a concentration of between about 0.5% and 3.0% or an equivalent amount of *Ruscus aculeatus* extract; a dill seed extract at a concentration of between about 1.0% and 5.0%; a dill seed oil at a concentration of between about 1.0% and 5.0%; and either an EGCG at a concentration of between about 1.0% and 5.0% or an equivalent amount of white/green tea extract.

In some embodiments, the composition comprises inactive ingredients including: water; a glycerin; a cetyl alcohol; a coconut oil; an olive oil; a jojoba oil; a glyceryl stearate; a paraben such as a methyl paraben, an ethyl paraben, or a poly paraben; a sodium benzoate, a vitamin E, a hydroxymethyl cellulose, a hyaluronic acid, a propylene glycol, a disodium EDTA, and a carbomer.

In addition to the facial mask, some embodiments include other physical means to provide electric currents to promote transcutaneous absorption of the composition. In some embodiments, the first lifting strap, the second lifting strap, or both the first lifting strap and the second lifting strap are configured to provide electric currents. In some embodiments, the electric currents are micro-currents and are generated by a battery or similar current-providing means. The current-providing means, in some embodiments, is incorporated within or coupled to the facial mask. In some embodiments, a separate current-providing means is electrically coupled to elements of the facial mask. In some embodiments, a natural passive current is provided by a grounding means. When grounding means are utilized, they may be connected to a grounding member that is connected to the earth via grounded wires directly into the earth or indirectly via the grounded receptacle of a standard electrical outlet. Further, the facial mask may comprise electrically conductive materials or means within the facial mask without a grounding member attached to the facial mask. In this case, the conductive materials may contact second or subsequent conductive means that is connected to a grounded cord such as, but not limited to, a grounded pillow case or grounded pillow case insert which may be connected to a grounding member to the earth directly or indirectly. Simply, the facial tissues may be conductively connected to the conductive facial mask which in turn is conductively connected to a pillow case, pad, or other means by physical approximation or touching of the facial mask and the pillow case or other means, and the pillow case or other means are then connected to the ground source by a grounding wire, In this latter configuration, the user will not experience the "tethering" effect of being directly connected to a grounding member and may experience more comfort and freedom of movement while sleeping. Moreover, this latter configuration will allow the user to arise from bed, or from wherever they may be, without having to detach or uncouple the grounding member or means from the mask. They may then return and become grounded again by simply placing their head on the pillow case or other secondary grounding means.

Grounding, or "earthing," is a term that describes efforts to achieve health benefits from walking outside while barefoot or while wearing electrically conductive footwear such as leather, or when performing indoor activities (working, sleeping, etc.) while connected to conductive systems that transfer the Earth's electrons from the ground via a ground wire or other conductive means into the body. Reported health benefits include stabilization of the immune system, enhanced heart rate variability, enhanced healing, diminished inflammation, normalized blood pressure, diminished cortisol levels, improved mood, diminished delayed onset muscle soreness after strenuous exercise, increased capillary blood flow and protection against dementia, amongst many other health benefits. Many of the grounding devices currently available act by grounding the user with a sheet to sleep upon, pads, straps, or adhesive electrodes that are connected to the ground via wires or through the ground terminal of an electrical outlet. While these means may help with restoring our natural neutral electric potential, humans have connected with the ground mostly through their feet while awake sixteen hours a day. They slept on nonconductive cellulose in the form of dried leaves, straw, and other nonconductive plant material to cushion them from the earth. Hence, although grounding during sleep may have some benefits, it does not mimic the evolution of humans being primarily grounded while awake and primarily through the feet when awake. We evolved by being grounded primarily through channels which originate in the soles of our feet. This normal, natural method of grounding a human from a positive electric potential to the neutral electric potential of the earth and ridding one of the unnatural positive voltage that accumulates from various causes (including electromagnetic frequencies) during waking hours and through the feet has been limited severely in the past 50 years with the conversion of footwear from a conductive leather to nonconductive synthetic products.

Leather is somewhat conductive, and humans have used animal skins for footwear for eons. Especially with a bit of moisture from the environment or just from perspiration on the soles of the feet or both, footwear of leather and other animal products provides enough electrical conductivity to adequate ground the wearer. However, since leather does not provide complete dryness, becomes wet, is expensive, and is difficult to configure a traction tread, amongst other drawbacks, the vast majority of footwear utilizes other nonconductive man-made materials at least for the sole. This essentially insulates the user from the earth and the many readily encountered conductive substances covering the earth and prevents the ingress of beneficial electrons into the body.

Humans have been connected to the earth naturally for 500,000 years and have used leather and animal skins on their feet. Our body has evolved to be grounded through the feet during that time. The recent change in the construction of most footwear which effectively insulates a person from the ground and the dramatic increase in electromagnetic fields has caused the human body to be limited in its ability to function optimally. Voltages up to about 7 volts have been measured in individuals in different environments while wearing nonconductive footwear and the voltage approximated zero a short time after they were connected to a ground wire. Because of the presence of electrical appliances, computers, cell phones, modems, unshielded electrical wiring, amongst other unavoidable electromagnetic fields, all humans except those in the most remote and isolated locations off the electrical grid are subject to and carry positive voltages in their body without realizing it. These abnormal, unnatural inherent positive voltages alter the body's release of hormones, neurotransmitters, electrical impulses, cellular permeability, mitochondrial activity, and many other functions. The body may cope and remain mostly healthy, but since the systems are not operating at peak capacity and peak performance in a finely tuned manner, there is a moderate chance an electrochemical reaction will incite a cascade of events that results in inflammation, which is the root cause of most all illnesses and maladies and responsible for all the conditions mentioned previously. The change in the construction of footwear over the past 60 years prevents most humans from achieving a neutral electrical state. One's overall appearance, including facial characteristics and appearance, does reflect one's overall health and well-being including one's psychological condition, immune system, sympathetic/parasympathetic nervous system balance, mood, and many other conditions that may be improved by grounding. Hence, it is an object of this invention to provide a means of grounding the facial tissues to support healing of facial tissues while providing positive systemic health benefits to the user that may be reflected in the health of the facial tissues as well as their general overall health. This means of grounding is especially important as our natural means of connecting with the earth through our feet has been severely limited, if not eliminated, over the past 50 years because of non-conductive footwear.

An affordable grounding device that provides grounding benefits while sleeping and promotes facial rejuvenation, vitality, mental clarity, diminished anxiety, and health is described. One embodiment of this device is constructed to be worn while in bed, driving a car, or during sitting while at a computer workstation, amongst others. In some embodiments, the device is electrically coupled to the earth by wires and a grounding rod placed in the earth or by a connection, which are be wires, in some embodiments; to the ground terminal or a third hole of an electrical outlet. In some embodiments, the grounding device extends over a portion of the face and is anchored over the ears and then cinched beneath the chin to secure it. In some embodiments, the grounding device is secured about the dorsal aspect of the head. Benefits provided by the grounding device include increased vascularity and healing to the facial tissues, focused grounding to the head and neck region including the brain, diminished snoring and obstructive sleep apnea, and others.

Although grounding one particular body part has been shown to be effective throughout the whole body, grounding closer to the area of desired effect has also been shown to be more effective when a specific outcome is desired or when the effects of grounding are desired to be maximized at a particular anatomical area. This has been documented by the inventor with different experiments and practiced by others. For example, to relieve or prevent delayed onset muscle soreness, some practitioners place a grounding electrode over the particular muscle group of interest rather than using a pad to sleep upon or a grounding electrode on one foot. Moreover, by utilizing an inexpensive voltmeter, one can easily determine that the voltage in the part of the body closest to the grounding source diminishes more than the voltage at the remote location. Hence, if one wished to normalize the voltage of the head and neck area, which includes the brain, one strategy may be to place the grounding source closer to those areas than simply having a grounding contact on an extremity or in contact with the torso. This device may have a more localized and focally greater grounding effect on the delicate tissues of the face and neck, the sinuses and nasopharynx, the oropharynx, scalp and neck muscles, the brain and other head and neck structures than a remote grounding location. This observation may be validated by the Inverse Square Law, which states that the intensity of a physical quantity is inversely proportional to the square of the distance from the source of that physical quantity. In layman's terms, this means the closer the grounding source, the effectiveness is increased by a factor of the square of the distance difference. Hence, in some embodiments, the benefits of grounding are focally delivered by the grounding device to the important facial structures to improve appearance; to the sinuses, nasopharynx and oropharynx to combat congestion, obstructive sleep apnea, and snoring; to the scalp and neck muscles to combat tension headaches and tension in general; to the ears to enhance hearing and diminish tinnitus; and to the brain to provide a host of positive benefits including better sleep, improved mood, augmented immune response, diminished seasonal affective disorder, and increased energy, amongst many other health benefits. These benefits may be provided directly to the head and neck area, but will positively affect other more remote areas of the body as well.

In some embodiments, the grounding device comprises a grounded skull cap. The thick bone of the skull, however, may not be as conductive as the soft tissues of the face and neck and the rather delicate bony structures at the base of the skull. Hence placing the grounding device over the very vascular facial structures and over the arteries of the neck may be more effective at grounding the tissues of the brain and head and neck.

In some embodiments, the facial mask, the first lifting strap, or the second lifting strap comprises a grounding surface electrically coupled to the skin of at least some of the user's face as well as the head and neck structures. In some embodiments, a grounding surface is on the middle one third of the user's face below the eyes and is anchored or held in place by a retention means placed over or around the ears or behind the head. In some embodiments, a grounding member is electrically coupled to the grounding device. In some embodiments, the grounding device is electrically coupled to a second grounding device or alternative electrically conductive object that is primarily or secondarily grounded, such as a pillow case or mat which contacts the grounding device. In some embodiments, the facial mask extends to the upper neck and/or chin to contact the skin in the submandibular region. In some embodiments, the grounding device is positioned over the carotid arteries located anteriorly in the upper neck region. These arteries carry blood and electrical charges to the brain where inflammation has been shown to cause a number of health issues, including immune disorders, depression, anxiety, and a host of others. In fact, upregulation of the microglia of the brain is an important central inflammatory reaction which may be at the root of many more chronic and even acute illnesses and conditions. The anti-inflammatory properties of grounding hence may be concentrated in the head and neck region wherein the grounding device provides focal grounding in the head and neck region.

An additional benefit of the grounding device is lifting the tissues of the cheeks or other tissues while in place and providing the grounding benefits, as in the facial mask described herein. Supporting facial structures may cause the user to have a more youthful appearance as the combined effects of grounding and support provide a more refreshed skin appearance with less sagging of the facial tissues which may occur with normal aging.

In some embodiments, grounding, lifting support, and elastin stimulation/reparation are provided simultaneously. If the facial mask is utilized only during sleep, the uplifting of the facial tissues may not completely persist through the day as gravity will cause the tissues to sag towards their original position when the individual is erect. However, human tissue has somewhat of a memory and some of the lifting of the tissues will persist despite the effects of gravity when not using the facial mask. This is especially true with repeated use. If one uses the facial mask only during sleep for 7 hours a night, that computes to 49 hours each week, 210 hours each month, and 2,555 hours each year. This also equates to slightly less than ⅓ of one's existence. This time is enough to effect substantive change in the skin, subcutaneous tissues, connective tissues, etc., that may result in an improved appearance especially when combined with either a elastin stimulating or reparative substance or the focal anti-inflammatory effects of focal grounding on the tissues of the head and neck or both.

The facial mask is formed in one of several configurations, according to the embodiment of the invention. In some embodiments, the supportive facial mask comprises the first lifting strap and the grounding device that conductively contacts the tissues of at least one of the face and neck. Some embodiments of the facial remodeling system comprise the grounding device. Some embodiments of the facial remodeling system do not comprise the grounding device.

Figure 1:
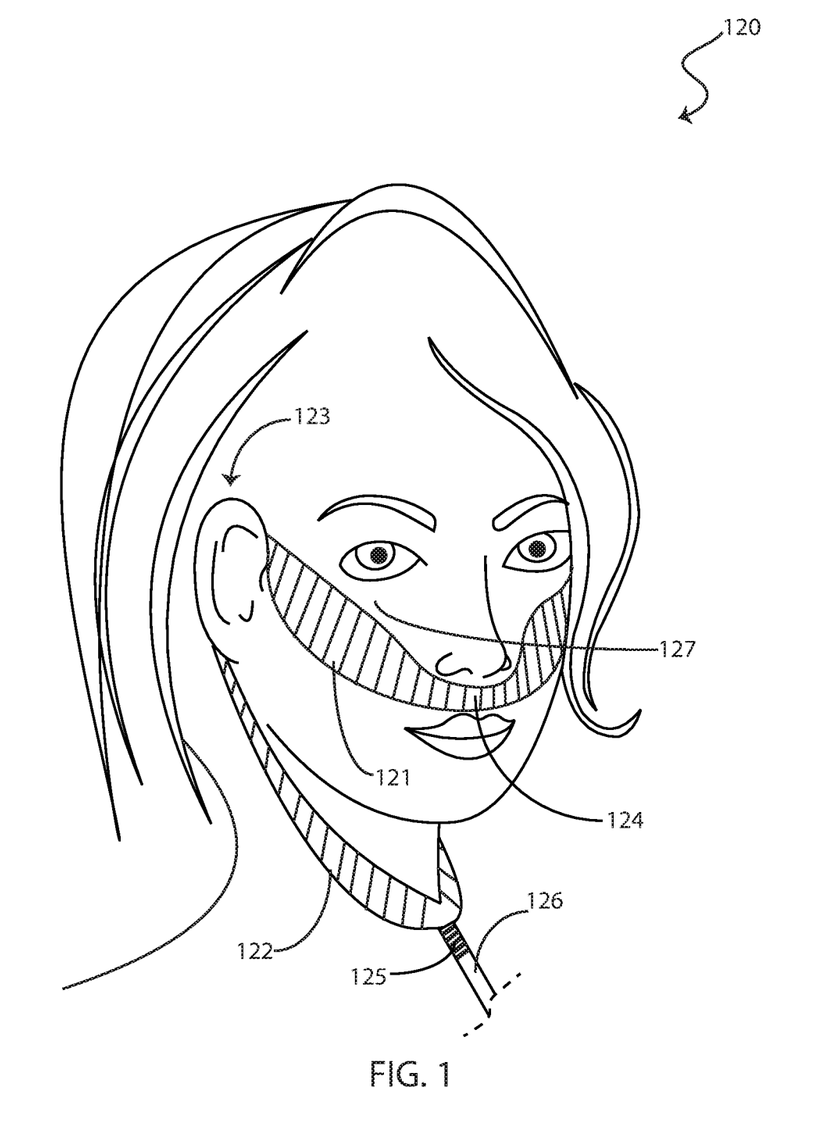
FIG. 1 a side perspective view of a facial mask worn by a user.

FIG. 1 is a side perspective view of a facial mask worn by a user. FIG. 1 shows facial mask 120 with grounding device is configured as the first lifting strap, the second lifting strap, or an additional strap configured to support the facial skin and tissue. This is detailed in FIG. 1 which is a partial side view of a face of a subject and the instant invention, a facial mask 120, which comprises a nose to ear portion forming a first lifting strap 121, an upper neck portion forming a second lifting strap 122, an ear section 123 coupled between first lifting strap 121 and second lifting strap 122, a central portion 124 coupled between two first lifting straps 121, a first securing means 125 configured to couple a grounding member 126 to second lifting strap 122, as shown in FIG. 1.

First lifting strap (nose to ear portion) 121, in some embodiments, is not straight but rather comprises a downward or caudal-directed convex curve and contacts the skin of the cheek tissues below a zygomatic eminence (cheek bone) 127. First lifting strap 121 (nose to ear portion 121), in some embodiments, is formed from an elastomer and configured to lift the cheek tissues when worn. The lower or caudal portion of first lifting strap (nose to ear portion) 121 is reinforced so that it compressively lifts the tissue, in some embodiments. The upper or cephalad portion of first lifting strap (nose to ear portion) 121 is be more lax than the lower or caudal portion so that it does not compress the tissue that is being compressively lifted by the lower or caudal portion, in some embodiments. In some embodiments, central portion 124 is not elastic at all so as to prevent elevation of the lower lip. A non-elastic central portion 124 may not cause any traction on the upper lip when the entire device is worn, which is a desired action.

In this example, and all example embodiments shown by the several drawing figures, the means to secure the lifting strap means to the face comprises first securing means 125 positioned under the chin after being secured over the ears or may comprise a different securing mechanism which may extend to and be secured about the dorsal aspect of the head.

Figure 2:
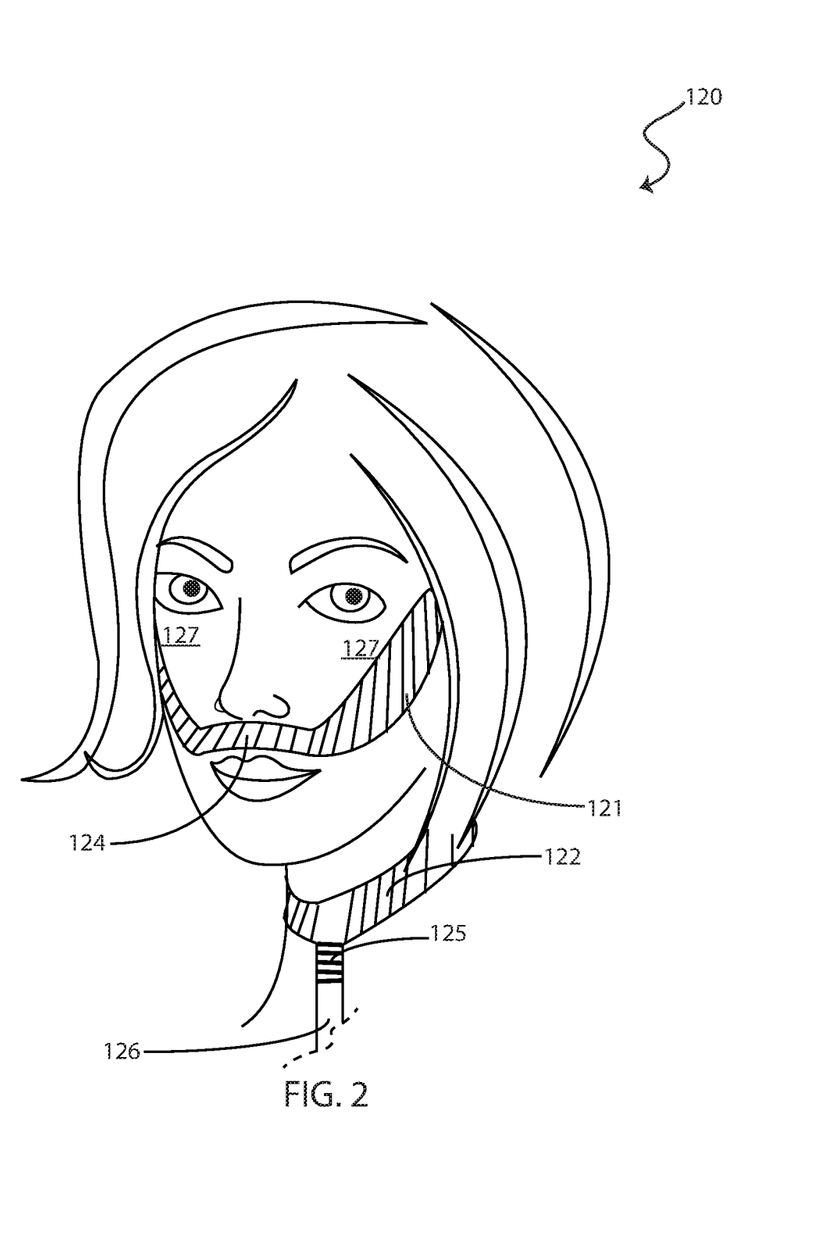
FIG. 2 is a front perspective view of a facial mask worn by a user.

FIG. 2 is a front perspective view of a facial mask worn by a user. FIG. 2 shows facial mask 120 worn on the user's face. It may be desirable that facial mask 120 is configured such that first lifting strap 121, second lifting strap 122, or both first lifting strap 121 and second lifting strap 122 are positioned below the area of the cheeks. A curved configuration of first lifting strap (nose to ear portion) 121 of facial mask 120 is configured, as shown by FIG. 2 and in some other embodiments, to accommodate this, as a straight strap or straight nose to ear portion would traverse the cheeks and compress them rather than supporting them. Accordingly, a first width of first lifting strap (nose to ear portion) 121 must be adequate to support the tissues without creating a furrow in the skin of the face. In some embodiments, the first width is in a range of from about 2 millimeters (mm) to about 10 centimeters (cm). In some embodiments, the first width is between about 2.0 cm and about 5.0 cm. Some or all elements of facial mask 120 may comprise an elastomeric element, but particularly first lifting strap (nose to ear portion) 121. The elastomeric element(s) may be placed elsewhere however. Elasticity combined with the downward curvature of first lifting strap (nose to ear portion) 121 tend, in some embodiments, to lift the cheek tissues.

Grounding may be provided or may not be provided. In some embodiments of facial mask 102 wherein grounding is provided, facial mask 102 is grounded by one of several means, including but not limited to utilizing an electrically conductive material for the entire facial mask 120, utilizing conductive materials to connect different conductive materials at different locations within facial mask 120 to the grounding source, utilizing a conductive material which is added to the non-conductive facial mask to provide grounding, or other means. Moreover, focal grounding may be provided in specific areas and not throughout facial mask 120. For example, conductive means may be provided only in first lifting strap (nose to ear portion) 121 where the facial tissues are supported, over the carotid arteries in second lifting strap (neck portion) 122 to deliver focal grounding over the blood supply to the brain, over the upper lip to combat the aging of tissues in that location, or the like.

Focal grounding in the mid-neck over the carotid arteries may be of particular importance as the carotid body mechanism (carotid glomus or glomus caroticum), is located at the branching of the common carotid artery into the internal carotid artery and external carotid artery. The carotid body contains specialized cells and a rich network of chemoreceptors and nerve fibers that control many body functions including oxygen, carbon dioxide and hydrogen ion regulation, respiration, heart beat and rhythm, multiple sympathetic and parasympathetic functions, amongst others. Focally grounding the carotid body area and returning that area to a naturally grounded state, is a purpose of this invention, and may affect a number of organ systems and their interaction with other organ systems. A conductive means may be provided to target only certain anatomical locations or several anatomical locations concurrently.

Figure 3:
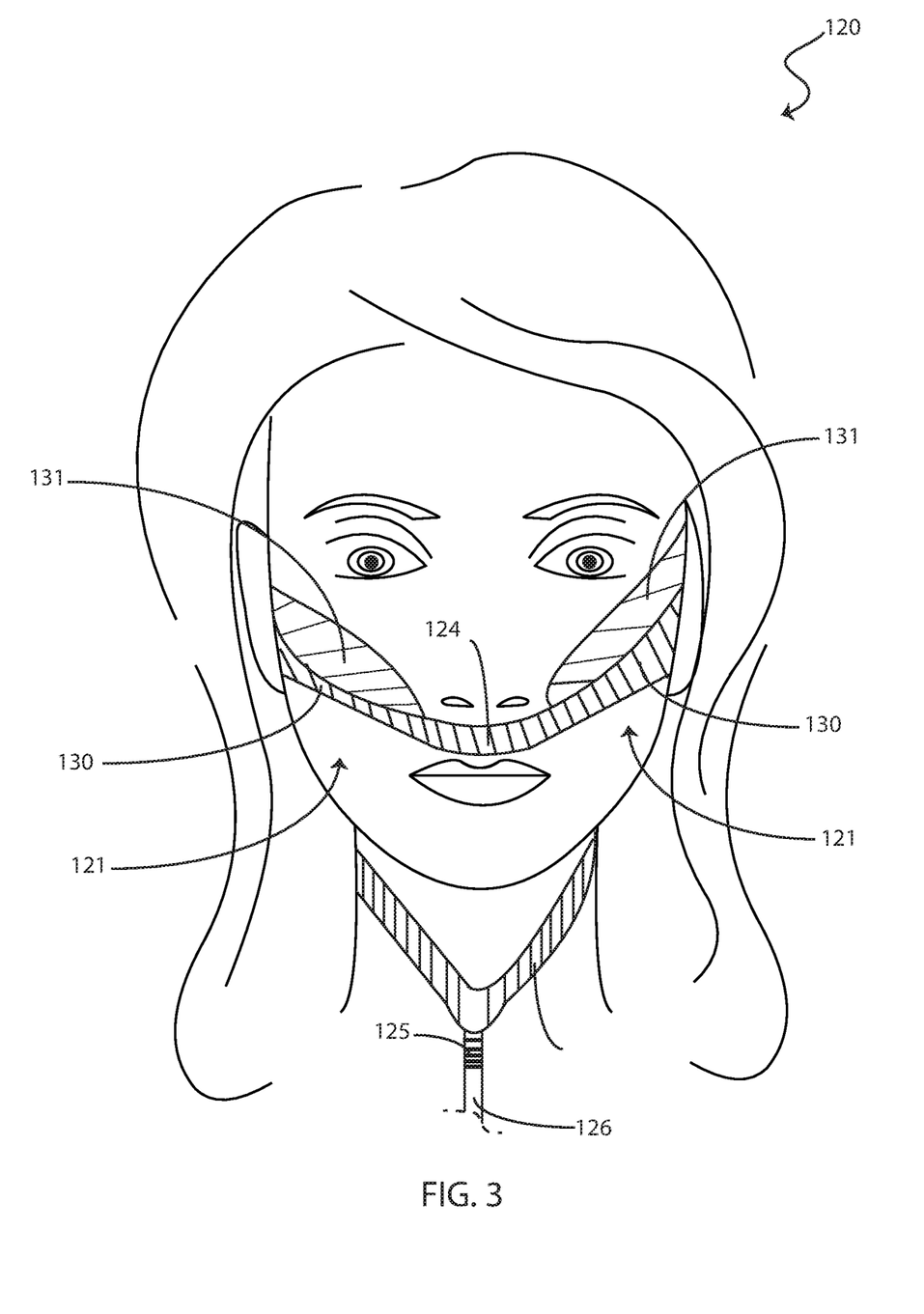
FIG. 3 is an additional front perspective view of a facial mask worn by a user.

FIG. 3 is an additional front perspective view of a facial mask worn by a user. FIG. 3 demonstrates a partial frontal view of an alternative embodiment of facial mask 120. In this, and some other embodiments, first lifting strap 121 comprises a first part 130 coupled to a second part 131. First part 130, in some embodiments, is configured to simultaneously support and ground. In some embodiments, first part 130 is configured to support. In some embodiments, second part 131 is configured to ground without giving support or significant compression but with contact of the tissues of the cheek area wherein the configuration will provide focal grounding to the skin and tissues of the cheeks without compressing the cheek tissues as first part 130 of first lifting strap 121 delivers support and lifting of the cheek tissues.

Figure 4:
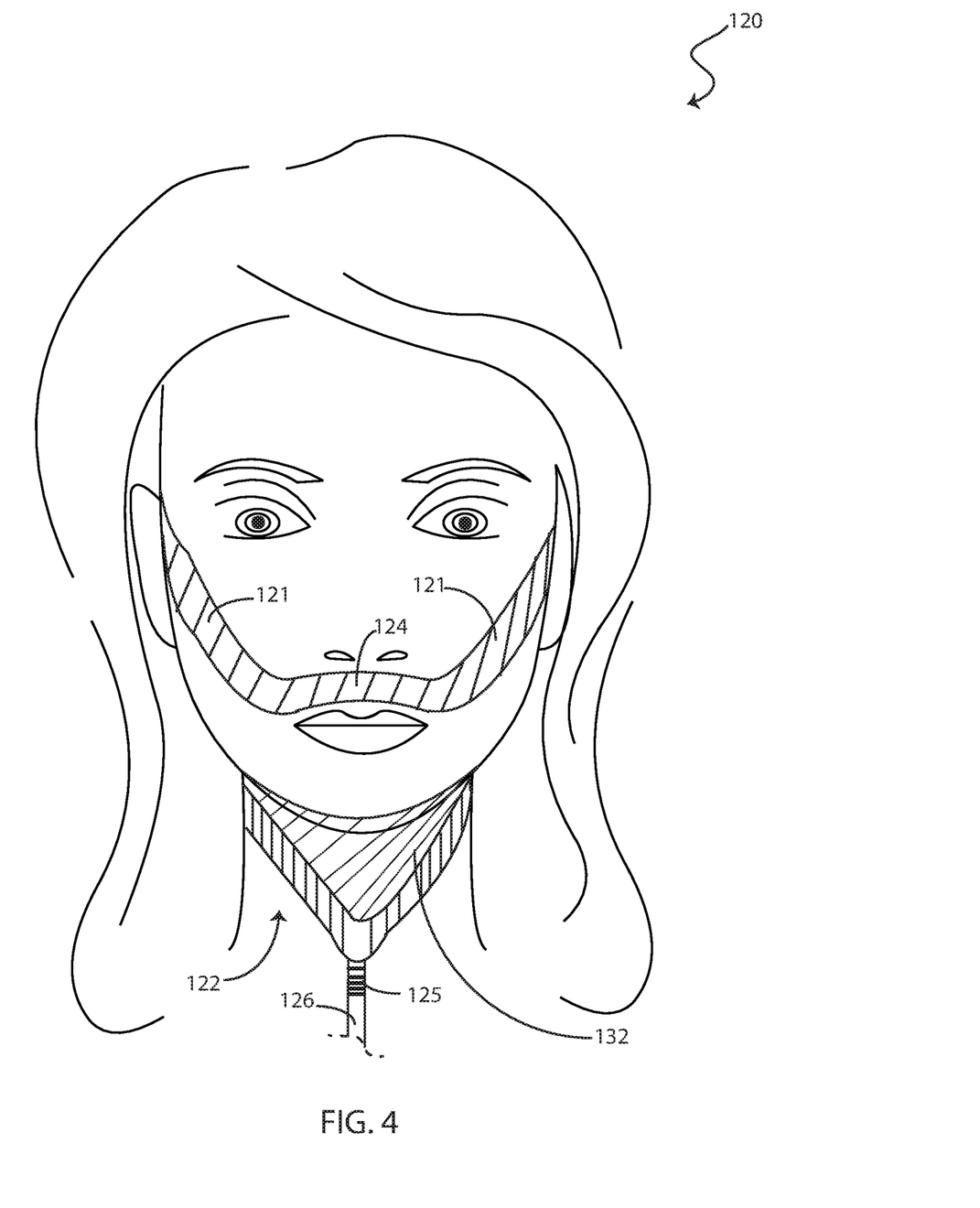
FIG. 4 is a front perspective view of a facial mask worn by a user.

FIG. 4 is a front perspective view of a facial mask worn by a user. FIG. 4 shows an alternative embodiment of facial mask 120, provide means to support with or without focally grounding to the tissues of the upper neck. Second lifting strap 122 of facial mask 120, in some embodiments, is configured to contact an increased surface area of skin of the upper neck. In some embodiments, second lifting strap 122 comprises a third part 132, as shown by FIG. 4. Third part 132 may provide grounding, support, or compression to additional tissues, including the submandibular tissues where jowls develop, turkey neck occurs, and crepe like skin is common. Third part 132 is comprised by facial mask 120 having any one or combination of elements listed herein.

The combination of focal grounding and compression with a composition to stimulate elastin and other components or diminish the degradation of elastin and other components of tissues, along with providing structural physical support for these delicate tissues is configured to work harmoniously to reduce and at least partially correct the oxidative stress reactions in the tissues which result in the aging changes and to at least partially re-mold the tissues to a more youthful appearance.

Figure 5:
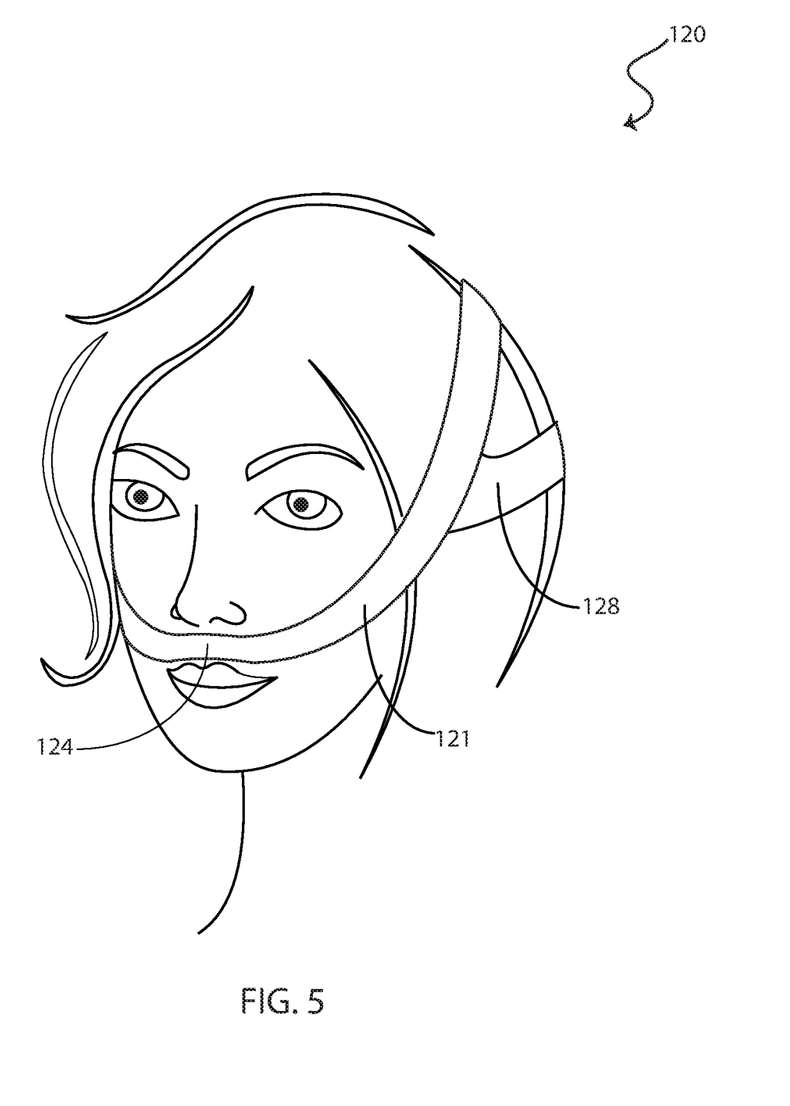
FIG. 5 is a perspective view of an attachment means for a facial mask.

FIG. 5 is a perspective view of an attachment means for a facial mask. The embodiments described herein may be secured to the user by the example means shown above or by other alternative means or configurations including, but not limited to, the configuration in FIG. 5. FIG. 5 shows a second securing means 128 configured to secure the first lifting strap 121 to the head and to provide upward lifting of the tissues of the cheeks at the same time. Facial mask 120, is configured to only provide focal grounding without providing any structural support to the soft tissues. Facial mask 120 may or may not be grounded, according to the embodiment of the invention. Grounding member 126 (See FIGS. 1, 2, & 4), if comprised by the embodiment, is electrically coupled to second securing means 128 of facial mask 120. In some embodiments, grounding member 126 is electrically coupled to a grounded body, such as a pad or pillow case, by simple physical contact with that grounded body. Grounding member 126 is also electrically coupled to any grounding means, many examples of which are discussed herein.

The components defining any system and device for facial remodeling may be formed of any of many different types of materials or combinations thereof that can readily be formed into shaped objects provided that the components selected are consistent with the intended operation of a system and device for facial remodeling. For example, the components may be formed of: rubbers (synthetic and/or natural) and/or other like materials; glasses (such as fiberglass) carbon-fiber, aramid-fiber, any combination thereof, and/or other like materials; polymers such as thermoplastics (such as ABS, Fluoropolymers, Polyacetal, Polyamide; Polycarbonate, Polyethylene, Polysulfone, and/or the like), thermosets (such as Epoxy, Phenolic Resin, Polyimide, Polyurethane, Silicone, and/or the like), any combination thereof, and/or other like materials; composites and/or other like materials; metals, such as zinc, magnesium, titanium, copper, iron, steel, carbon steel, alloy steel, tool steel, stainless steel, aluminum, any combination thereof, and/or other like materials; alloys, such as aluminum alloy, titanium alloy, magnesium alloy, copper alloy, any combination thereof, and/or other like materials; any other suitable material; and/or any combination thereof.

Furthermore, the components defining any system and device for facial remodeling may be purchased pre-manufactured or manufactured separately and then assembled together. However, any or all of the components may be manufactured simultaneously and integrally joined with one another. Manufacture of these components separately or simultaneously may involve extrusion, pultrusion, vacuum forming, injection molding, blow molding, resin transfer molding, casting, forging, cold rolling, milling, drilling, reaming, turning, grinding, stamping, cutting, bending, welding, soldering, hardening, riveting, punching, plating, and/or the like. If any of the components are manufactured separately, they may then be coupled with one another in any manner, such as with adhesive, a weld, annealing, a fastener (e.g. a bolt, a nut, a screw, a nail, a rivet, a pin, and/or the like), wiring, any combination thereof, and/or the like for example, depending on, among other considerations, the particular material forming the components. Other possible steps might include sand blasting, polishing, powder coating, zinc plating, anodizing, hard anodizing, and/or painting the components for example.

Figure 6:
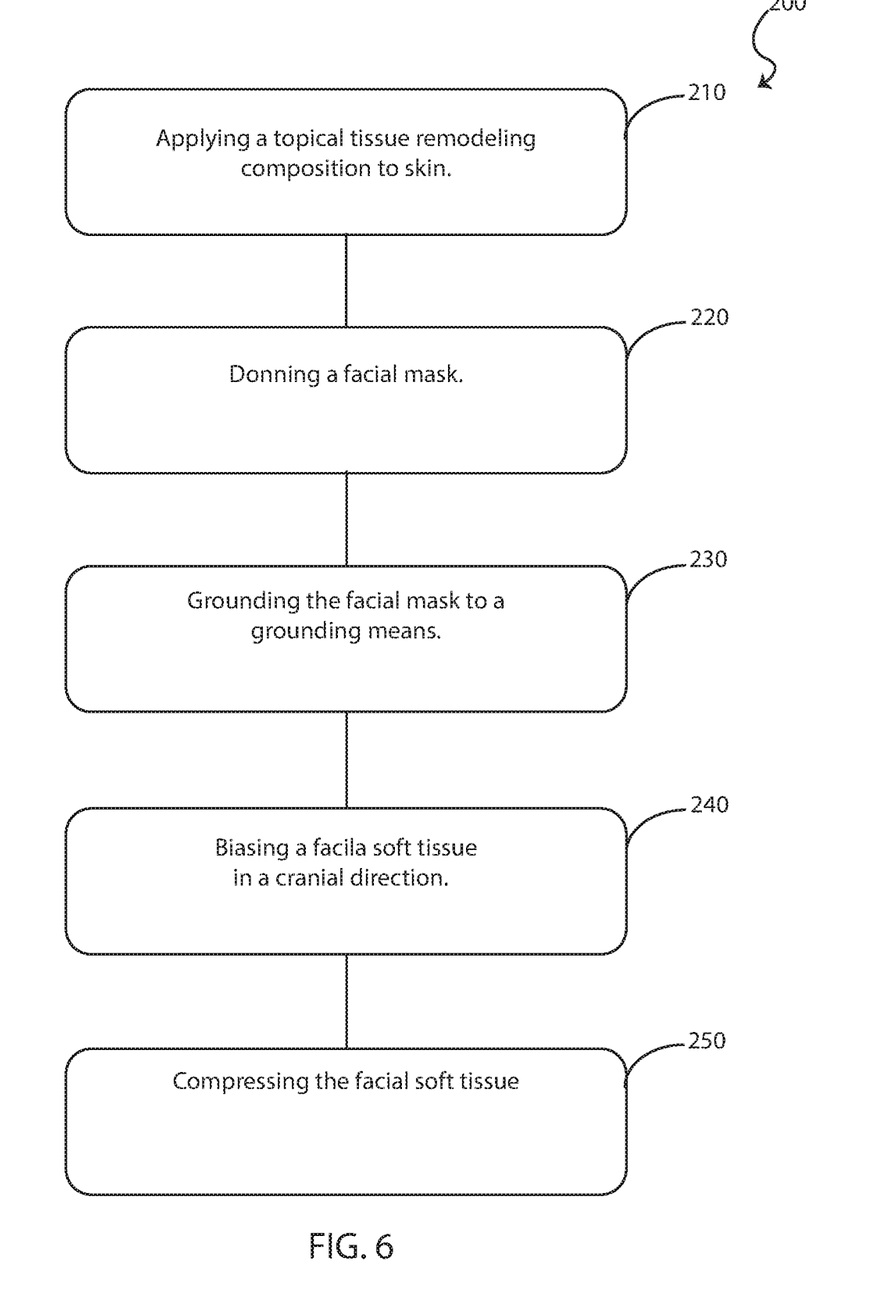
FIG. 6 is a flowchart of a method of forming a system of facial remodeling.

FIG. 6 is a flowchart of a method of using a system and device for facial remodeling. FIG. 6 shows a method 200 comprising an applying step 210, a donning step 220, a grounding step 230, a biasing step 240, and a compressing step 250.

Applying step 210 comprises applying a topical tissue remodeling composition to skin. In some embodiments, the composition comprises an elastin-enhancing compound. In some embodiments, the composition comprises a plurality of elastin-enhancing compounds. An elastin-enhancing compound is a compound or mixture of compounds known or used to either inhibit elastin degradation in a tissue, such as a skin tissue or a subcutaneous connective tissue, or to promote elastin synthesis in a skin tissue of a subcutaneous connective tissue. The compound may be a currently known compound, or a compound discovered at some future time to inhibit elastin degradation, promote elastin synthesis, or both. Some examples of elastin-enhancing compounds are listed herein.

Donning step 220 comprises donning a facial mask. In some embodiments, donning step 220 comprises looping an ear section over each of the user's ears, causing a first lifting strap coupled to the ear section on each side of the user's face to contact an area of skin of the user's face. In some embodiments, the area of skin includes skin overlying the zygomatic eminence. In some embodiments, donning step 220 comprises applying a second lifting strap on each side of the user's face or neck to contact an area of skin of the user's face or neck.

Grounding step 230 comprises grounding the facial mask to a grounding means. In some embodiments, grounding step 230 comprises coupling a grounding member to the facial mask. In some embodiments, grounding step 230 comprises coupling the grounding member to the first lifting strap. It is understood that the grounding member is grounded by any suitable grounding means discussed herein, wherein the grounding member is electrically coupled, or "earthed," to the ground. Some embodiments of method 200 do not comprise grounding step 230.

Biasing step 240 comprises biasing a facial soft tissue in a cranial direction. In some embodiments, biasing step 240 is caused by an elastomeric member comprising the facial mask, such as an elastomeric first lifting strap or an elastomeric second lifting strap, for example.

Compressing step 250 comprises compressing a facial soft tissue. Similar to biasing step 240, in some embodiments, compressing step 250 is causes by an elastomeric member comprises the facial mask, or some element of the facial mask, as discussed herein. Some embodiments, of method 200 do not comprise compressing step 250.

A system, device, and method of facial remodeling are disclosed. The system combines a topical composition configured to restore elastin, hyaluronan, or both to the skin and subcutaneous soft tissues of the face and neck combined with a facial mask to support and, in some embodiment, compress the tissue, to enhance and preserve the tissue remodeling effects of the composition. In some embodiments, the device and method include a means for electrically grounding—"earthing"—the skin and soft tissues of the face, neck, and head.

The embodiments and examples set forth herein were presented in order to best explain the present invention and its practical application and to thereby enable those of ordinary skill in the art to make and use the invention. However, those of ordinary skill in the art will recognize that the foregoing description and examples have been presented for the purposes of illustration and example only. The description as set forth is not intended to be exhaustive or to limit the invention to the precise form disclosed. Many modifications and variations are possible in light of the teachings above without departing from the spirit and scope of the forthcoming claims.

What is claimed is:

1. A system of facial remodeling comprising:
a facial mask having a nose to ear portion and a central portion forming a first lifting strap;
a behind ear section coupled to the first lifting strap;
an upper neck portion forming a second lifting strap coupled to the behind ear section, wherein the first lifting strap and the second lifting strap are coupled together by the behind ear section; and
a tissue remodeling composition, wherein the facial mask is configured to support a facial tissue treated with the tissue remodeling composition.

2. The system of claim 1, wherein the facial mask comprises a grounding member coupled to the first lifting strap, wherein the grounding member is earthed to a grounded body by physical contact with the grounded body.

3. The system of claim 1, wherein the facial mask comprises a grounding member earthed to a grounding device.

4. The system of claim 1, wherein the facial mask comprises a securing means configured to couple a grounding member to the second lifting strap.

5. The system of claim 1, wherein the first lifting strap comprises an elastomeric element.

6. The system of claim 1, wherein the facial mask comprises an elastomeric element.

7. The system of claim 1, wherein the remodeling composition comprises:
an elastin-promoting compound;
a hyaluronan-promoting compound; and
a topical delivery vehicle.

8. The system of claim 7, wherein the elastin-promoting compound is at least one compound selected from the group of compounds consisting of: a ruscogenin at a concentration in a range between about 0.5 percent and 3.0 percent; a dill seed extract at a concentration in a range between about 1 percent and about 5 percent; and a dill seed oil at a concentration in a range between about 1 percent and 5 percent.

9. The system of claim 7, wherein the elastin-promoting compound is selected from the group of elastin-promoting compounds consisting of: *Ruscus aculeatus* extract; epigallocatechin-3-gallate; white tea extract; green tea extract; micronized purified flavonoid fraction; *Hedera helix* extract; hederagenin; palmitoyl pentapeptide-4; palmitoyl oligopeptide; and palmitoyl-tetrapeptide-7.

10. The system of claim 7, wherein the hyaluronan-promoting compound is selected from the group of hyaluronan-promoting compounds consisting of: glucosamine, palmitoyl pentapeptide-4; palmitoyl oligopeptide; palomitoyl-tetrapeptide-7; and ethoxyheptyl bicyclooctanone.

11. The system of claim 7, wherein the topical delivery vehicle is selected from the group of topical delivery vehicles consisting of: water; glycerin; cetyl alcohol; coconut oil; olive oil; jojoba oil; glyceryl stearate; a paraben; sodium benzoate; vitamin E; hydroxymethyl cellulose; hyaluronic acid; propylene glycol; disodium EDTA; and a carbomer.

12. The system of claim 1, wherein the first lifting strap comprises a caudal-directed convex curve.

13. The system of claim 1, wherein the first lifting strap has a width in the range of from about 2 mm to about 10 cm.

14. The system of claim 1, wherein the facial mask comprises an electrically conductive material.

15. A system of facial remodeling comprising:
- a facial mask having a nose to ear portion and a central portion forming a first lifting strap;
- a tissue remodeling composition, wherein the facial mask is configured to support a facial tissue treated with the tissue remodeling composition; and
- a grounding member coupled to the first lifting strap, wherein the grounding member is earthed to a grounded body by physical contact with the grounded body or earthed to a grounding device.

\* \* \* \* \*